United States Patent [19]

Harre et al.

[11] Patent Number: 4,709,077
[45] Date of Patent: Nov. 24, 1987

[54] 7-(ARYLOXY)-2-NAPHTHOXYALKANECARBOXYLIC ACID DERIVATIVES, PROCESSES FOR THE PREPARATION OF THESE COMPOUNDS, AS WELL AS AGENTS HAVING HERBICIDAL ACTIVITY CONTAINING THESE COMPOUNDS

[75] Inventors: Michael Harre; Hans-Rudolf Krüger; Friedrich Arndt; Reinhart Rusch, all of Berlin, Fed. Rep. of Germany

[73] Assignee: Schering Aktiengesellschaft, Berlin and Bergkamen, Fed. Rep. of Germany

[21] Appl. No.: 777,053

[22] Filed: Sep. 17, 1985

[30] Foreign Application Priority Data

Sep. 17, 1984 [DE] Fed. Rep. of Germany ....... 3434447
Jul. 15, 1985 [DE] Fed. Rep. of Germany ....... 3525562

[51] Int. Cl.⁴ .............................................. C07C 69/76
[52] U.S. Cl. .................................... 560/056; 562/466; 546/302; 71/94; 71/108; 71/109; 71/114; 558/411; 558/414; 558/252; 564/172; 564/173

[58] Field of Search ........................ 560/056; 562/466; 546/302; 71/94, 108, 109, 114; 558/411, 414, 252; 564/172, 173

[56] References Cited

U.S. PATENT DOCUMENTS 3,979,437 9/1976 Theissen ................................ 560/21

Primary Examiner—Paul J. Killos
Attorney, Agent, or Firm—Millen & White

[57] ABSTRACT

Novel 7-(Aryloxy)-2-naphthoxyalkanecarboxylic acid derivatives of the formula I

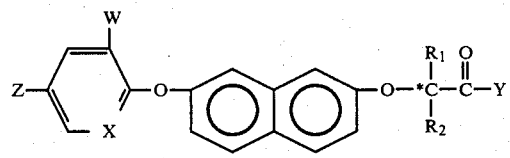

in racemic or separated isomeric form, have herbicidal activity.

64 Claims, No Drawings

7-(ARYLOXY)-2-NAPHTHOXYALKANECARBOXYLIC ACID DERIVATIVES, PROCESSES FOR THE PREPARATION OF THESE COMPOUNDS, AS WELL AS AGENTS HAVING HERBICIDAL ACTIVITY CONTAINING THESE COMPOUNDS

BACKGROUND OF THE INVENTION

This invention relates to novel racemic and isomeric 7-(aryloxy)-2-naphthoxyalkanecarboxylic acid derivatives, processes for their preparation, as well as herbicidal compositions based thereupon.

Other herbicidal active agents based on phenoxyalkanecarboxylic acid derivatives (Japanese Laid-Open Application No. 92,369/80) and based on phenoxybenzoic acid derivatives (U.S. Pat. No. 3,979,437) have been known. They are deficient however.

SUMMARY OF THE INVENTION

It is thus an object of this invention to provide novel active agents and a herbicide having superior properties which contains these active agents.

Upon further study of the specification and appended claims, further objects and advantages of this invention will become apparent to those skilled in the art.

These objects have been attained according to this invention by providing racemic and isomeric 7-(aryloxy)-2-naphthoxyalkanecarboxylic acid derivatives of Formula I

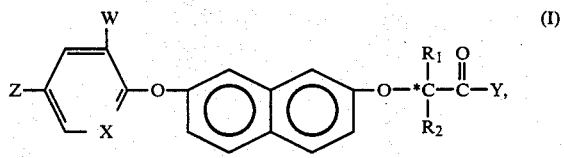

wherein
Z is hydrogen, halogen, $C_1$–$C_4$-alkyl, trihalomethyl or cyano,
W is hydrogen, halogen, $C_1$–$C_4$-alkyl, trihalomethyl or cyano,
X is —CH—, —C-halogen or —N—,
$R_1$ is hydrogen, $C_1$–$C_4$-alkyl or $C_1$–$C_4$-alkyl substituted by halogen,
$R_2$ is hydrogen, $C_1$–$C_4$-alkyl, or $C_1$–$C_4$-alkyl substituted by halogen,
Y is —$UR_3$ or

U is oxygen or sulfur,
$R_3$ is $C_1$–$C_{18}$-alkyl; $C_1$–$C_{18}$-alkyl substituted by halogen or $C_{1-4}$-alkoxycarbonyl or cyano or interrupted once or several times by oxygen or sulfur atoms; $C_{3-12}$-alkenyl; $C_{3-12}$alkynyl; $C_3$–$C_{12}$-cycloalkyl; phenyl; phenyl mono- or polysubstituted by halogen, $C_1$–$C_4$-alkyl, $C_1$–$C_4$-alkoxy, $C_1$–$C_4$-alkylthio, nitro, cyano or trifloromethyl; benzyl; benzyl mono- or polysubstituted by halogen, $C_1$–$C_4$-alkylthio, phenoxy, nitro, cyano or trofluoromethyl; a 5- to 6-membered heterocycle; hydrogen; an alkali metal atom; a corresponding equivalent of a bivalent metal; or an ammonium group

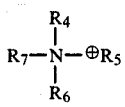

wherein $R_4$, $R_5$, $R_6$ and $R_7$ each independently is hydrogen; $C_1$–$C_6$-alkyl; $C_1$–$C_6$-alkyl substituted by hydroxy or $C_1$–$C_4$ alkoxy; or alkoxycarbonylalkyl

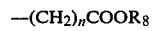

wherein
n is 1–4 and $R_8$ is $C_1$–$C_4$-alkyl; and
$R_9$ and $R_{10}$ each independently is hydrogen, $C_1$–$C_{18}$-alkyl, $C_2$–$C_8$-alkenyl, $C_2$–$C_8$-alkynyl, aryl-$C_1$–$C_3$-alkyl, $C_3$–$C_8$-cycloalkyl, $C_{1-4}$-alkoxycarbonyl-$C_{1-4}$-alkyl, $C_3$–$C_8$-cycloalkyl-$C_1$–$C_3$-alkyl, tetrahydrofurfuryl, or an aromatic hydrocarbon (aryl), wherein each of the rentioned $R_9$ and $R_{10}$ groups can be mono- or poly-substituted, identically or differently, by $C_1$–$C_6$-alkyl, halogen, $C_1$–$C_6$-alkoxy, phenoxy, CN, OH, $CH_2OH$, methylenedioxy, phenyl, $C_{2-4}$-alkynyl, nitro and/or trifluoromethyl, or $R_9$ and $R_{10}$ jointly with the connecting N atom form morpholino, piperidino or pyrrolidino.

DETAILED DISCUSSION

The R isomers as designated herein are understood to mean those optically active compounds having the R configuration at the asymmetrical carbon atom *C if $R_1$ and $R_2$ are not identical. Analogous remarks apply with respect to the S iosomers.

In all of the substituents in Formula I, the alkyl, alkenyl or alkynyl residues can be straight-chain or branched. Prefered halogen atoms throughout are chlorine or bromine; fluorine is also suitable. Non-limiting examples of suitable five- and six-membered heterocyclic residues include furan, pyran, pyrrole, pyrrolidine, pyrodine, piperidine, pyrazole, pyrazolidine, Pyrimidine, oxazolidine, oxazole, morpholine, thiazole and thioazolidine. Generally, suitable such heterocycles include those of 5 or 6 ring atoms, one, two or three of which are O, N and/or S, the remaining being C-atoms, and the rings being aromatic or aliphatic (preferably saturated). Generally, the nusber of halo substituents on the $C_{1-4(or\ 6)}$-alkyl groups is 1–3/C-atom; and the number of the CN substituent on the $C_{1-18}$-alkyl groups is 1/C-atom.

The number of interrupting oxa or S atoms in the $C_{1-18}$-alkyl groups in generally 1–4/group. The number of phenyl or benzyl substituents generally is 1–5 substituents/moiety. In $R_9/R_{10}$ the aryl portions are generally hydrocarbon and of 6–10 C-atoms, but also include heteroaryl, e.g., pyridyl. Generally, the number of $R_9/R_{10}$ substituents is 1–5.

Among the compounds of this invention, those are especially distinguished in their efficacy wherein, in Formula I, the substituent
Z is fluorine, chorine, bromine, hydrogen, cyano, trifluoromethyl, trichloromethyl, methyl, ethyl or isopropyl
W is fluorine, chlorine, bromine, hydrogen, cyano, trifluoromethyl, trichloromethyl, methyl, ethyl or isopropyl
X is C—H—, —C—F—, —C—Cl—, —C—Br— or N, Y is a residue $UR_3$ wherein U is an oxygen or sulfur atom, and $R_3$ is hydrogen, methyl, ethyl, 2,2,2-trifluoroethyl, propyl, isopropyl, butyl, allyl, propargyl, cyclohexyl, pentyl, hexyl, dodecyl, methoxyethyl, ethoxyethyl, benzyl, 4-chlorobenzyl, 4-nitrobenzyl, phenyl, 4-chlorophenyl, 4-nitrophenyl, 3-phenoxybenzyl, or an alkali metal atom, preferably a lithium, sodium or potassium atom, or a corresponding equivalent of a bivalent metal, e.g., zinc, manganese, calcium, magnesium or barium, or ammonium, ethylammonium, diethylammonium, triethylammonium, tetraethylammonium, tetrabutylammonium, or a 5- to 6-membered heterocyclic residue, e.g., furan, pyran, pyrrole, pyrrolidine, pyridine, piperidine, oxazolidine, oxazole, morpholine, thiazole, thiazolidine, wherein the residue is preferably linked via a carbon atom to the oxygen or sulfur binding the residue to the remainder of the molecule, or Y is a nitrogen atom substituted by $R_9$ and $R_{10}$ wherein $R_9$ and $R_{10}$, independently of each other, are hydrogen, methyl, ethyl, propyl, isopropyl, n-butyl, tert-butyl, 2,2-dimethyl-1-propyl, n-heptyl, n-nonyl, n-undecyl, n-octadecyl, 3-methylbutyl, 4-methyl-2-pentyl, isobutyl, 3,30dimethylbutyl, 20chloroethyl, 3-chloropropyl, 3-bromopropyl, 2-bromoethyl, 1-phenoxy-2-propyl, tetrahydrofurfuryl, ethoxycarbonylmethyl, cyanomethyl, 2,2-dimethoxyethyl, or 2-ethoxyethyl, cyclohexylmethyl, 4-cyanocyclohexylmethyl, 4-hydroxymethylcyclohexylmethyl, cycloheptylmethyl or cyclooctylmethyl or cyclopropylmethyl, 2-propenyl, 2-butenyl, 2-methyl-2-propenyl, 2-propynyl or 3-ethyl-1-pentyn-3-yl, as the aryl-$C_1$–$C_3$-alkyl residues, benzyl, 4-chlorobenzyl, 3-chlorobenzyl, 2-chlorobenzyl, 4-fluorobenzyl, 3-fluoro-benzyl, 2-fluorobenzyl, 4-methylbenzyl, 3-methylbenzyl, 2-methylbenzyl, 3,4-methylenedioxybenzyl, 2,4-dichlorobenzyl, 3,4-dichlorobenzyl, 4-methoxybenzyl, 3-methoxybenzyl, 2-methoxybenzyl, 2-pyridylmethyl, 3-pyridylmethyl, 4-pyridylmethyl, α,α-dimethylbenzyl, 1-phenylethyl, 2-phenylethyl, 1,2-diphenylethyl, 2,2-diphenylethyl, 4-fluoro-α-methylbenzyl, 3-phenylpropyl, cyclopropyl, cyclopentyl, cyclohexyl, 2-methylcyclohexyl, 3-methylcyclohexyl, 4-methylcyclohexyl, 1-ethynyl-cyclohexyl, cycloheptyl or cyclooctyl, as the aromatic hydrocarbon residues, phenyl, 3-chlorophenyl, 4-fluorophenyl, 2-methylphenyl, 3-methylphenyl, 4-methylphenyl, 1-naphthyl, 2-methoxyphenyl, 3-methoxy-phenyl or 4-nitrophenyl, an $R_1$ is hydrogen, $C_{1-4}$-alkyl, or $C_{1-4}$-alkyl substituted by halogen, and $R_2$ is hydrogen, $C_{1-4}$-alkyl, or $C_{1-4}$-alkyl substituted by halogen.

Preferred compounds are 2-(R)-[7-(Aryloxy)-2-naphthoxy]propanoic acid derivatives of the Formula

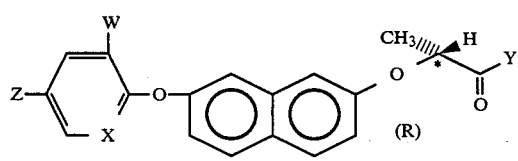

wherein

Z and W, independently of each other, are hydrogen, halogen, $C_1$–$C_4$-alkyl, trihalomethyl or cyano X is CH—, C-halogen, preferably C-fluoro, C-chloro or C-bromo, or a nitrogen atom, Y is $UR_3$, wherein U is an oxygen or sulfur atom. and $R_3$ is $C_1$–$C_{18}$-alkyl substituted by halogen or cyano or interrupted once or several times by oxygen or sulfur, $C_{3-12}$-alkenyl, $C_3$–$C_{12}$-alkynyl, $C_3$–$C_{12}$-cycloalkyl, phenyl or benzyl which is unsubstituted or mono- or poly-substituted by halogen, $C_1$–$C_4$-alkyl, $C_1$–$C_4$-alkoxy, $C_1$–$C_4$-alkythio, nitro, cyano or trifluoromethyl, or a 5- to 6-membered heterocyclic residue as above; hydrogen, an alkali metal atom, preferably a lithium, sodium or potassium atom, or a corresponding equivalent of a bivalent metal, preferably zinc, manganese, calcium, magnesium or barium or an ammonium ion of the formula

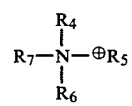

wherein $R_4$, $R_5$, $R_6$ and $R_7$ are, independently of one another, hydrogen, alkyl of up to 6 carbon atoms or halogen-, hydroxy- or alkoxy-substituted alkyl of up to 6 carbon atoms, or carbalkoxyalkyl $[-(CH_2)_nCOOR_8]$ wherein n is 1–4 and $R_8$ is $C_1$–$C_4$-alkyl, or Y is

wherein $R_9$ and $R_{10}$ are identical or different and each is hydrogen, $C_1$–$C_{18}$-alkyl, substituted $C_1$–$C_{18}$-alkyl, $C_2$–$C_8$-alkenyl or -alkynyl, optionally substituted aryl-$C_1$–$C_3$-alkyl, optionally substituted $C_3$–$C_8$-cycloaliphatic hydrocarbyl, optionally substituted $C_3$–$C_8$-cycloalkyl-$C_1$–$C_3$-alkyl, an aromatic hydrocarbon residue optionally mono- or polysubstituted by $C_1$–$C_6$-alkyl and/or halogen and/or $C_1$–$C_6$-alkoxy and/or nitro and/or trifluoromethyl, or $R_9$ and $R_{10}$ together with the connecting N atom form morpholino, piperidino or pyrrolidino or Y can also be

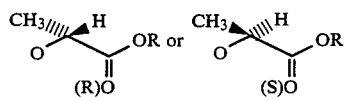

wherein

R is $C_{1-4}$-alkyl, and the asymmetrical carbon atom has the R or S configuration.

The compounds of this invention can be prepared conventionally by (a) reacting compounds of Formula II

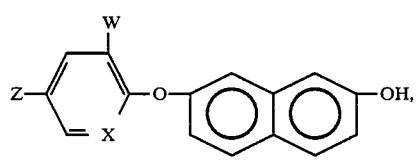

with compounds of Formula III

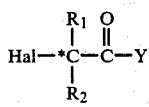 (III)

optionally in the presence of a diluent and/or an acid-neutralizing medium; or
(b) reacting compounds of Formula IV

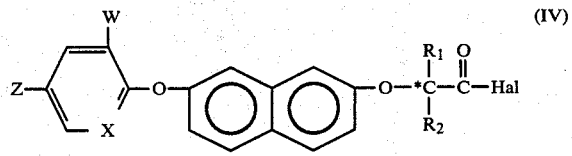 (IV)

with compounds of Formula V

H—Y  (V)

optionally in the presence of a diluent and/or an acid-neutralizing medium; or
(c) reacting compounds of Formula VI

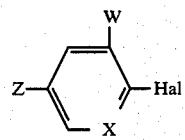 (VI)

with compounds of Formula VII

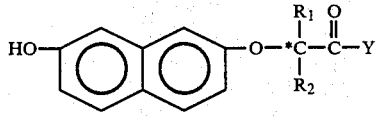 (VII)

optionally in the presence of a diluent and/or an acid-neutralizing medium; or
(d) reacting compounds of Formula VIII

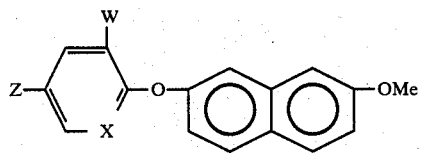 (VIII)

with compounds of Formula III

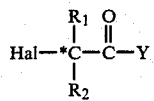 (III)

optionally in the presence of a diluent, wherein
Z, W, X, R$_1$, R$_2$ and Y are as defined above, Hal is halogen and Me is an alkali metal atom; or
(e) reacting a compound of Formula II wherein Z, W and X are as defined above with S isomers of propanoic acid derivatives of Formula IX

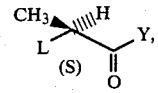 (IX)

wherein
Y is as defined above and
L is the residue O—SO$_2$—R$_{11}$ wherein R$_{11}$ is a methyl or 4-methylphenyl group, optionally in the presence of an acid acceptor, and/or optionally in the presence of a diluent; or
(f) reacting R configured compounds of Formula X

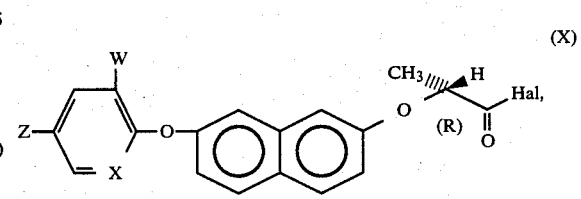 (X)

wherein
Z, W and X are as defined above and Hal stands for a halogen atom,
with a compound of Formula V

H—Y  (V)

wherein Y is as defined above; or
(g) reacting a compound of Formula VI

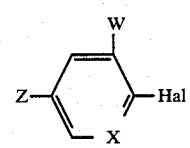 (VI)

wherein
Z, W, X and Hal are as defined above, with an R configured compound of Formula XII

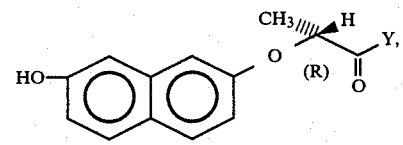 (XII)

wherein Y is as defined above; or
(h) reacting a compound of Formula VIII

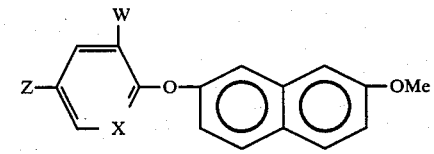 (VIII)

wherein
Z, W and X are as defined above and
Me is an alkali metal ion,
with S isomers of the propanoic acid derivatives of above-identified Formula IX, optionally in the presence of an acid acceptor and/or optionally in the presence of a diluent.

Reaction version (a) is preferably conducted in the Presence of a diluent. Any of the inert solvents can be utilized for this purpose. Non-limiting examples of such solvents or diluents include water, aliphatic, alicyclic and aromatic hydrocarbons, each of which can optionally be chlorinated, such as hexane, cyclohexane, petroleum ether, ligroin, benzene, toluene, xylene, methylene chloride, chloroform, carbon tetrachloride, ethylene chloride, trichloroethylene, chlorobenzene; ethers, such as diethyl ether, methyl ethyl ether, diisopropyl ether, dibutyl ether, dioxiane and tetrahydrofuran; ketones, such as acetone, methyl ethyl ketone, methyl isopropyl ketone and methyl isobutyl ketone; nitrile, such as acetonitrile, propionitrile; alcohols, such as methanol, ethanol, isopropanol, butanol and ethylene glycol; esters, such as ethyl acetate and amyl acetate; acid amides, such as dimethylformamide and dimethylacetamide; sulfones and sulfoxides, such as dimethyl sulfoxide and sulfolane; and bases, such as pyridine.

Reaction version (a) is furthermore preferably performed in the presence of an acid-neutralizing medium. Non-limiting examples of such acid-neutralizing media include hydroxides, carbonates, hydrogen carbonates and alcoholates of alkali metals, and tertiary amines, such as triethylamine, diethylamine and pyridine.

Reaction version (a) can be conducted within a wide temperature range. In general, the reaction is performed at a temperature of $-20°$ C. to the boiling point of the reaction mixture, preferably 0° C. to 150° C. This version of the reaction is preferably conducted under ambient pressure, although it can also be effected under elevated or reduced pressure.

When conducting reaction version (b), one of the non-limiting solvents or diluents described above for reaction version (a) is preferably employed to obtain the final product with high purity in a high yield.

Reaction versions (b) and (c) take place analogously to version (a) preferably with the use of diluents and acid-neutralizing media under reaction conditions as described above.

Reaction version (d) is likewise performed under the reaction conditions described for (a), preferably using one of the diluents disclosed therefor.

In the preparation of the R isomers of the diphenyl ether derivatives according to Formula I of the process (e) according to this invention, the use of S enantiomers of the propanoic acid derivatives of Formula IX is required since during the course of the reaction a Walden inversion takes place on the asymmetrical carbon atom. The S enantiomers of the propanoic acid derivatives of Formula IX rotate the plane of polarized light toward the left.

Process version (e) is preferably conducted in the presence of a diluent. Any of the inert solvents can be utilized for this purpose, as also cited in connection with process version (a). The other process parameters of version (e), such as use of acid-neutralizing medium, temperature, and pressure, are as described for version (a). The same also holds true with respect to process versions (f) and (g).

Reaction version (h) can likewise be performed under the reaction conditions as set forth above for process version (a). However, when conducting process version (h), one of the solvents disclosed for process version (a) is preferably employed, but first the compound of Formula IX is prepared by treating the corresponding compound of formula II with a strong base, such as, for example, sodium hydride or potassium hydride.

The presence of a reaction catalyst can be of advantage in conducting all reaction versions. Suitable non-limiting catalysts included potassium iodide and onium compounds, such as quaternary ammonium, phosphonium and arsonium, compounds, as well as sulfonium compounds. Likewise suited are polyglycol thers, especially cyclic ones, such as, for example, 18-crown-6 and tertiary amines, e.g., tributylamine. Preferred compounds are quaternary ammonium compounds e.g., benzyltriethylammonium chloride and tetrabutylammonium bromide.

The compounds of this invention preparable according to the above-described methods can be isolated from the reaction mixtures with the aid of the conventional processes, for example by removing the solvent employed by distillation under normal or reduced pressure, by precipitation with water, by extraction etc. An increased degree of purity can usually be achieved by purification with the aid of column chromatography as well as by fractional distillation or crystallization.

The compounds of this invention normally represent almost colorless and odorless fluids, as well as crystals which are sparingly soluble in water, sparingly soluble in aliphatic hydrocarbons, such as petroleum ether, hexane, pentane and cyclohexane, readily soluble in halogenated hydrocarbons, such as chloroform, methylene chloride and carbon tetrachloride, aromatic hydrocarbons, such as benzene, toluene and xylene, ethers, such as diethyl ether, tetrahydrofuran and dioxane, carboxylic acid nitriles, such as acetonitrile, alcohols, such as methanol and ethanol, carboxylic acid amides, such as dixethylformamide, and sulfoxides, such as dimethyl sulfoxide.

The active agents are normally obtained during the synthesis as a racemic misture and can be separated into the optical antipodes in a manner known pe se, for example by fractional crystallization, unless isomeric starting material is intentionally employed from the beginning.

Those compounds of Formula I wherein $R_3$ is a metal atom or an amxonium group are present as salts which are dissociated in an aqueous solution into the corresponding ions.

The starting compounds for preparing the compounds of this invention, such as, for example, the S isomers of the propanoic acid derivatives of Formula IX, are known per se or can be produced in accordance with conventional methods from conventional starting materials.

The compounds of this invention are distinguished by a general herbicidal effect, directed not only specifically against grasses; in this respect, they are surprisingly superior to conventional active agents of analogous constitution. A special advantage is that these compounds, in applied amounts of about 0.1 kg of active agent/ha, inhibit or even prevent the coring up of monocotyledonous and dicotyledonous weeds in agricultural cultivated areas, without damaging the cultivated plants up to applied amounts of about 5 kg of active agent/ha.

Weeds of this type include but are not limited to, for example, Viola, Galium, Veronica, Centaurea, Ipomoea, Abutilon, Sesbania, Datura, Chrysanthemum, Polygonum, Sida, Xanthium, Amaranthus, Setaria, Digitaria, Echinochloa and Alopecurus. Consequently, these can be advantageously combatted selectively by the post-germination method in cultivated stands of, e.g., and not limited to, wheat, barley, rye, oats, corm, rice, soybeans, cotton, etc.

Several active compounds are also suitable for desiccation and defoliation, especially those compounds of Formula I wherein Z is trihalomethyl, W is halogen, X is —CH—, $R_1$ is hydrogen, $R_2$ is methyl and Y is $OR_3$ ($R_3 = C_{1-18}$-alkyl or $C_{1-18}$-alkyl interrupted by an oxygen atom). The applied amounts for herbicidal effect generally range in conventional dependence on the end purpose from 0.05 to 5 kg of active compound/ha, but even higher application quantities can be utilized if desired. The timing of application also conventionally depends on the object and also on the climatic conditions. In general, the compounds of this invention when used as a herbicide are utilized analogously to the use of the known herbicide acifluorfen (U.S. Pat. No. 3,979,437).

The compounds of this invention can be utilized either individually or in admixture with one another or with other active agents. Optionally, other plant-protective agents or pesticides can be added, depending on the purpose for the treatment. When it is desired to broaden the spectrum of activity, other biocides can also be added. Herbicidally active mixing partners suitable in this connection include for example, the active agents listed in Weed Abstracts, vol. 34, No. 3 (1985) under the heading "Lists of common names and abbreviations employed for currently used herbicides and plant growth regulators in weed abstracts".

Also usable are agents which are not phytotoxic and, as is known, can result in a synergistic rise in efficacy when combined with herbicides and/or growth regulators, e.g., inter alia, surfactants, emulsifiers, solvents, and oily additives. Furthermore, suitable as mixing partners are phospholipids, e.g., those from the group of phosphatidyl choline, the hydrogenated phosphatidyl cholines, phosphatidyl ethanolamine, the N-acyl-phosphatidyl ethanolamines, phosphatidyl inositol, phosphatidyl serine, lysolecithin, and phosphatidyl glycerol, The active compounds of this invention are suitably employed in the form of preparations, e.g., powders, dusting agents, granulated materials, or solutions with the addition of liquid and/or solid vehicles, and/or diluents and, if desired, wetting agents and/or adhesive agents. Suitable non-limiting liquid vehicles include, for example, water, methanol, ethanol, dimethylformamide or dimethyl sulfoxide. Non-limiting solid vehicles suitable for this purpose include mineral earths, e.g., "Tonsil", silica gel, talc, or kaolin, etc. Non-limiting surfactants include: cationic anionic and nonionic tensides, e.g., calcium lignosulfonate, polyethylene alkyl phenyl ether, naphthalenesulfonic acids and their salts, formaldehyde condensates, fatty alcohol sulfates, as well as substituted benzenesulfonic acids and their salts, etc.

The proportion of the active compound or compounds in the various preparations can vary within wide limits. The agents contain, for example, about 10–90% by weight of active compounds, approximately 90–10% by weight of liquid or solid vehicles, as well as optionally up to 40% by weight of surfactants.

The agents can be applied in the usual manner.e.g,, dusting, spraying, painting, etc. for example with water as the vehicle in spraiying fluid quantities of about 100–1,000 l/ha.

Use of the agents in the so-called "low-volume" or "ultra-low-volume" method is likewise feasible, as is their application in the form of so-called microgranules, (see for references, e.g., Matthews, G.A., Pesticide application methods, Longman Inc., N.Y. 1979).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following are exemplary of preparations:

A. SPRAYABLE POWDER (a)
- 40% by weight of active compound
- 25% by weight of clay minerals
- 20% by weight of silicic acid
- 10% by weight of ligninsulfonate
- 5% by weight of surfactants based on a mixture of the calcium salt of lignosulfonic acid with alkyl phenol polyglycol ethers (b)
- 25% by weight of active compound
- 60% by weight of kaolin
- 10% by weight of "Wesseling"
- 5% by weight of surfactants based on the sodium salt of N-methyl-N-oleyl-taurine and on the calcium salt of lignosulfonic acid B. PASTE
- 45% by weight of active compound
- 5% by weight of sodium aluminosilicate
- 15% by weight of cetyl polyglycol ether with 8 moles of ethylene oxide
- 2% by weight of spindle oil
- 10% by weight of polyethylene glycol
- 23% by weight of water C. EMULSION CONCENTRATE
- 25% by weight of active compound
- 15% by weight of cyclohexanone
- 55% by weight of xylene
- 5% by weight of a mixture of nonylphenyl polyoxyethylene or calcium dodecylbenzenesulfonate The following examples demonstrate preparations of the compounds according to this invention.

EXAMPLE 1 (Version a)

2-[7-(2-Chloro-4-trifluoromethylphenoxy)-2-naphthoxy]propanoic Acid Ethyl Ester

Starting Materials

| | | |
|---|---|---|
| 6.14 g | (18.12 mmol) | 7-(2-chloro-4-trifluoromethyl-phenoxy)-2-hydroxynaphthalene |
| 2.51 g | (18.12 mmol) | potassium carbonate |
| 2.6 ml | (19.9 mmol) | 2-bromopropanoic acid ethyl ester |
| 150 ml | | 2-butanone |

Procedure

The starting materials are suspended in the cited solvent and refluxed for 6.5 hours. The hot solution is filtered, concentrated and chromatographed on silica gel (hexane/ethyl acetate 9:1).

Yield: 6.1 g = 77% of theory.

$n_D^{20}$: 1.5630.

| Analysis | C | H | Cl | F |
|---|---|---|---|---|
| Calculated: | 60.21% | 4.13% | 8.08% | 12.99% |
| Found: | 59.91% | 4.20% | 8.14% | 12.83% |

EXAMPLE 2 (Version b)

2-?
7-(2-Chloro-4-trifluoromathylphenoxy)-2-naphthoxy]-propanoic Acid Ethoxyethyl Ester

Starting Materials

| 3.6 g | (8.39 mmol) | 2-[7-(2-chloro-4-trifluoromethyl-phenoxy)-2-naphthoxy]propanoic acid chloride |
|---|---|---|
| 0.9 ml | (9.23 mmol) | 10% excess 2-ethoxyethanol |
| 1.3 ml | (9.23 mmol) | triethylamine |
| 20 ml | | tetrahydrofuran |
| 0.25 g | | 4-dimethylaminopyridine |

Procedure

2-Ethoxyethanol, triethylamine and 4-dimethylaminopyridine are combined and the acid chloride dissolved in 20 ml of tetrahydrofuran is add-d dropwise thereto under ice cooling.

The mixture is stirred for 2 hours, suctioned off, and rinsed with tetrahydrofuran. The filtrate is concentrated and chromatorgraphed on silica gel (hexane/ethyl acetate 9:1).

Yield: 2.43 g=60% of theory.
$n_D^{20}$: 1.5540.

| Analysis | C | H | Cl | F |
|---|---|---|---|---|
| Calculated: | 59.70% | 4.59% | 7.34% | 11.80% |
| Found: | 59.73% | 4.58 | 7.24% | 12.07% |

EXAMPLE 3 (Version c)

2-[ 7-(3-Chloro-5-trifluoromethyl-2-pyridyloxy)-2-naphthoxy]propanoic Acid Ethyl Ester

Starting Materials

| 2.51 g | (9.64 mmol) | 2-(7-hydroxynaphthyl-2-oxy)propanoic acid ethyl ester |
|---|---|---|
| 2.29 g | (10.6 mmol) | 2,3-dichloro-5-trifluoromethylpyridine |
| 1.46 g | (10.4 mmol) | potassium carbonate |
| 100 ml | | dimethylformamide |

Procedure 2.51 g (9.65 mmol) of 2-(7-hydroxynaphthyl-2-oxy)-propanoic acid ethyl ester and 1.46 g (10.4 mmol) of $K_2CO_3$ are heated in 100 ml of dimethylformamide to 60° C. and, via a dropping funnel, 2.29 g (10.6 mmol) of 2,3-dichloro-5-trifluoromethylpyridine, dissolved in a small amount of dimethylformamide, is gradually added thereto. The mixture is agitated for 4 hours at 60° C., the dimethylformamide is removed under vacuum and the residue chromatographed on silica gel (hexane/ethyl acetate 9:1).

Yield: 2.98 g=70% of theory.
$n_D^{20}$: 1.5640.

| Analysis | C | H | N | Cl | F |
|---|---|---|---|---|---|
| Calculated: | 57.35% | 3.90% | 3.18% | 8.06% | 12.96% |
| Found: | 57.55% | 3.85% | 2.68% | 8.05% | 12.39% |

EXAMPLE 4 (Version d)

2-[7-(2-Chloro-4-trifluoromethylphenoxy)-2-naphthoxy]isovaleric Acid Ethyl Ester

Starting Materials

| 3.0 g | (8.85 mmol) | 7-(2-chloro-4-trifluoromethylphenoxy)-2-hydroxynaphthalene |
|---|---|---|
| 0.21 g | (8.85 mmol) | sodium hydride, 55% strength |
| 1.85 g | (8.85 mmol) | 2-bromoisovaleric acid ethyl ester |
| 30 ml | | N,N—dimethylformamide |

Procedure

At 20° C., 7-(2-chloro-4-trifluoromethylphenoxy)-2-hydroxy-naphthalene is taken up in the above-mentioned solvent. At this temperature, the sodium hydride is added in incremental portions. After evolution of hydrogen can no longer be observed, 2-bromoisovaleric acid ethyl ester is added dropwise thereto. The misture is then further stirred for 3 hours at 60° C.

The mixture is stirred into 500 ml of water, extracted with methylene chloride, the organic phases are washed with water, dried with magnesium sulfate, and concentrated. The crude product is chromatographed on silica gel (eluent: hexane/ethyl acetate 9:1).

Yield: 1.4 g=34% of theory.
$n_D^{20}$: 1.5521.

| Analysis | C | H | Cl | F |
|---|---|---|---|---|
| Calculated: | 61.73% | 4.75% | 7.60% | 12.21% |
| Found: | 62.03% | 4.97% | 7.60% | 12.18% |

Further compounds according to this invention can be prepared in an analogous fashion:

| Example No. | Name of Compound | Version | Physical Constant |
|---|---|---|---|
| 5 | 2-[7-(5-Trifluoromethyl-2-pyridyloxy)-2-naphthoxy]propanoic acid ethyl ester | c | mp: 61–63° C. |
| 6 | 2-[7-(2-Chloro-4-trifluoromethylphenoxy)-2-naphthoxy]propanoic acid 2-methoxyethyl ester | a | $n_D^{20}$: 1.5586 |
| 7 | 2-[7-(2-Chloro-4-trifluoromethylphenoxy)-2-naphthoxy]propanoic acid methyl ester | b | $n_D^{20}$: 1.5696 |
| 8 | 2-[7-(2-Chloro-4-trifluoromethylphenoxy)-2-naphthoxy]propanoic acid | a | mp: 150° C. |

-continued

| Example No. | Name of Compound | Version | Physical Constant |
|---|---|---|---|
| 9 | 2-[7-(2-Chloro-4-trifluoromethylphenoxy)-2-naphthoxy]propanoic acid 3-phenoxybenzyl ester | b | $n_D^{20}$: 1.5965 |
| 10 | 2-[7-(2-Chloro-4-trifluoromethylphenoxy)-2-naphthoxy]propanoic acid propargyl ester | b | $n_D^{20}$: 1.5705 |
| 11 | 2-[7-(2-Chloro-4-trifluoromethylphenoxy)-2-naphthoxy]propanoic acid, sodium salt | a | mp: 150° C. |
| 12 | 2-[7-(2-Chloro-4-trifluoromethylphenoxy)-2-naphthoxy]propanoic acid n-butyl ester | b | $n_D^{20}$: 1.5542 |
| 13 | 2-[7-(2-Chloro-4-trifluoromethylphenoxy)-2-naphthoxy]propanoic acid allyl ester | b | $n_D^{20}$: 1.5641 |
| 14 | 2-[7-(2-Chloro-4-trifluoromethylphenoxy)-2-naphthoxy]propanoic acid phenyl ester | b | mp: 90–93° C. |
| 15 | 2-[7-(2-Chloro-4-trifluoromethylphenoxy)-2-naphthoxy[thiopropanoic acid S—benzyl ester | b | $n_D^{20}$: 1.6052 |
| 16 | 2-[7-(2-Chloro-4-trifluoromethylphenoxy)-2-naphthoxy]thiopropanoic acid S—ester | b | $n_D^{20}$: 1.5871 |
| 17 | 2-[7-(2-Chloro-4-trifluoromethylphenoxy)-2-naphthoxy]propanoic acid cyclohexyl ester | b | $n_D^{20}$: 1.5582 |
| 18 | 2-[7-(2-Chloro-4-trifluoromethylphenoxy)-2-naphthoxy]propanoic acid 2-methylphenyl ester | b | $n_D^{20}$: 1.5823 |
| 19 | 2-[7-(2-Chloro-4-trifluoromethylphenoxy)-2-naphthoxy]propanoic acid 2-methylbutyl ester | b | $n_D^{20}$: 1.5484 |
| 20 | 2-[7-(2-Chloro-4-trifluoromethylphenoxy)-2-naphthoxy]propanoic acid 3-bromopropyl ester | b | $n_D^{20}$: 1.5671 |
| 21 | 2-[7-(2-Chloro-4-trifluoromethylphenoxy)-2-naphthoxy]propanoic acid amide | b | mp: 115° C. |
| 22 | 2-[7-(2-Chloro-4-trifluoromethylphenoxy)-2-naphthoxy]propanoic acid ethylamide | b | mp: 112° C. |
| 23 | 2-[7-(2-Chloro-4-trifluoromethylphenoxy)-2-naphthoxy]propanoic acid diethylamide | b | mp: 100° C. |
| 24 | 2-[7-(2-Chloro-4-trifluoromethylphenoxy)-2-naphthoxy]propanoic acid anilide | b | mp: 146° C. |
| 25 | 2-[7-(2-Chloro-4-trifluoromethylphenoxy)-2-naphthoxy]propanoic acid n-butylamide | b | mp: 83° C. |
| 26 | 2-[7-(2-Chloro-4-trifluoromethylphenoxy)-2-naphthoxy]propanoic acid di-n-butylamide | b | $n_D^{20}$: 1.5580 |
| 27 | 2-[7-(2-Chloro-4-trifluoromethylphenoxy)-2-naphthoxy]propanoic acid 2-cyanoethyl ester | b | $n_D^{20}$: 1.5656 |
| 28 | 2-[7-(2-Chloro-4-trifluoromethylphenoxy)-2-naphthoxy]propanoic acid N—(ethoxycarbonylmethyl)amide | b | mp: 112° C. |
| 29 | 2-[7-(2-Chloro-4-trifluoromethylphenoxy)-2-naphthoxy]propanoic acid N—(1-methoxycarbonylethyl)amide | b | glass |
| 30 | 2-[7-(2-Chloro-4-trifluoromethylphenoxy)-2-naphthoxy]thiopropanoic acid S—(ethoxycarbonyl)methyl ester | b | $n_D^{20}$: 1.5698 |
| 31 | 5-O—[2-[7-(2-Chloro-4-trifluoromethyl-phenoxy)-2-naphthoxy]propanoic acid (1,2:3,4-bis-O—isopropylidene)]xylityl ester | b | glass |
| 32 | 2-[7-(2-Chloro-4-trifluoromethylphenoxy)-2-naphthoxy]butanoic acid ethyl ester | a | $n_D^{20}$: 1.5586 |
| 33 | 2-[7-(2-Chloro-4-trifluoromethylphenoxy)-2-naphthoxy]-2-methylpropanoic acid ethyl ester | a | $n_D^{20}$: 1.5572 |
| 34 | 2-(R,S)—[7-(2-Chloro-4-trifluoromethyl-phenoxy)-2-naphthoxy]propanoic acid [1-(S)—ethoxycarbonylethyl]ester | | $n_D^{20}$: 1.5481 |
| 35 | 2-(R,S)—[7-(2-Chloro-4-trifluoromethyl-phenoxy)-2-naphthoxy]propanoic acid [1-(R)—ethoxycarbonylethyl]ester | | $n_D^{20}$: 1.5502 |
| 36 | 2-[7-(4-Trifluoromethylphenoxy)-2-naphthoxy]-propanoic acid ethyl ester | | $n_D^{20}$: 1.5551 |
| 37 | 2-[7-(2-Chloro-4-trifluoromethylphenoxy)-2-naphthoxy]propanoic acid n-propyl ester | | $n_D^{20}$: 1.5590 |
| 38 | 2-[7-(2-Chloro-4-trifluoromethylphenoxy)-2-napthoxy]propanoic acid (2,2,2-trifluoro)ethyl ester | | mp: 72° C. |
| 39 | 2-[7-(2-Chloro-4-trifluoromethylphenoxy)-2-naphthoxy]propanoic acid furfuryl ester | | $n_D^{20}$: 1.5740 |

EXAMPLE 40

Under exclusion of moisture, 6 g of $K_2CO_3$ and 10 g of "Siccon", suspended in 200 ml of dimethyl sulfoxide (DMSO), are agitated overnight. Then 6.02 g of 2-(2-chloro-4-trifluoromethylphenoxy)-7-hydroxynaphthanlene is added thereto and the mixture is stirred for one hour at room temperature. At room temperature, a solution of 5 g of 2-(S)-(p-tolylsulfonyloxy)propanoic acid ethyl ester in DMSO is gradually added dropwise to the reaction mixture and the latter is agitated for 2 hours (TLC control). The mixture is then suctioned off by way of "Celite", the filtrate being extracted. The combined ether phases are washed with NaCl solution, dried over MgSO₄, and evaporated. Column chromatography on silica gel (hexane/ethyl acetate 9:1), thus obtaining 2.43 g of 2-(R)-[7-(2-chloro-4-trifluoromethylphenoxy)-2-naphthoxy? propanoic acid ethoxyethyl ester (60% of theory).

$n_D^{20}$: 1.5549.

$\alpha_D^{20}$: +51.4° (c=0.500, CHCl₃).

Further compounds of this invention can be prepared analogously:

| Example | Compound | Version | $n_D^{20}$/mp °C. | Opt. Rotation Value |
|---|---|---|---|---|
| 42 | 2-(R)—[7-(3-Chloro-5-trifluoromethyl-2-pyridyloxy)-2-naphthoxy]propanoic acid ethyl ester | b | 1.5633 | +61.9° (0.50) |
| 43 | 2-(R)—[7-(2-Chloro-4-trifluoromethyl-phenoxy)-2-naphthoxy]propanoic acid 2-methoxyethyl ester | b | 1.5514 | +50.4° (0.505) |
| 44 | 2-(R)—[7-(2-Chloro-4-trifluoromethyl-phenoxy)-2-naphthoxy]propanoic acid methyl ester | b | 1.5648 | +57.7° (0.540) |
| 45 | 2-(R)—[7-(2-Chloro-4-trifluoromethyl-phenoxy)-2-naphthoxy]propanoic acid | b | 51° C. | +37° (0.50) |
| 46 | 2-(R)—[7-(2-Chloro-4-trifluoromethyl-phenoxy)-2-naphthoxy]propanoic acid propargyl ester | b | 1.5606 | +67.3° (0.52) |
| 47 | 2-(R)—[7-(2-Chloro-4-trifluoromethyl-phenoxy)-2-naphthoxy]propanoic acid n-butyl ester | b | 1.5524 | +62.5° (0.52) |
| 48 | 2-(R)—[7-(2-Chloro-4-trifluoromethyl-phenoxy)-2-naphthoxy]propanoic acid allyl ester | b | 1.5633 | +53.9° (0.515) |
| 49 | 2-(R)—[7-(2-Chloro-4-trifluoromethyl-phenoxy)-2-naphthoxy]propanoic acid 2,2,2-trifluoroethyl ester | b | 1.5346 | +50.9° (0.530) |
| 50 | 2-(R)—[7-(2-Chloro-4-trifluoromethyl-phenoxy)-2-naphthoxy]propanoic acid isopropyl ester | b | 1.5493 | +39.2° (0.510) |
| 51 | 2-(R)—[7-(2-Chloro-4-trifluoromethyl-phenoxy)-2-naphthoxy]propanoic acid n-propyl ester | b | 1.5562 | +65° (0.500) |
| 52 | 2-(R)—[7-(2-Chloro-4-trifluoromethyl-phenoxy)-2-naphthoxy]propanoic acid [1-(S)—ethoxycarbonylethyl] ester | b | 1.5409 | +49.2° (0.520) |
| 53 | 2-(R)—[7-(2-Chloro-4-trifluoromethyl-phenoxy)-2-naphthoxy]propanoic acid [1-(R)—ethoxycarbonylethyl] ester | b | 1.5442 | +76.2° (0.505) | tography on silica gel, eluent hexane/ethyl acetate 9:1, yields 2-(R)-[7-(2-chloro-4-trifluoromsthylphenoxy)-2-naphthoxy? propanoic acid ethyl ester.

Yield: 7 g=89% of theory.

$n_D^{20}$: 1.5630.

$\alpha_D^{20}$: +56.1° (c=0.57, CHCl₃).

EXAMPLE 41

0.9 ml of 2-ethoxyethanol (10% excess), 1.3 ml of triethylamine, and 0.25 g of 4-dimethylaminopyridine are combined and 3.6 g of 2-(R)-[7-(2-chloro-4-trifluoromethylphenoxy)-2-naphthoxy]propanoic acid chloride, dissolved in 20 ml of tetrahydrofuan, is added dropwise under ice cooling. The mixture is stirred for 2 hours, suctioned off, and washed with tetrahydrofuran. The filtrate is concentrated and chromatographed on The following examples demonstrate the utilization of the compounds according to the invention, in the from of the above-mentioned preparations.

EXAMPLE 54

In a greenhouse, the compounds of this invention recited in the table were sprayed in an application quantity of 3.0 kg of active compound/ha, emulsified in 500 liters of water/ha, on Brassica*) and Matricaria**) as the test plants in the post-germination rethod. Three weeks after treatment, the result of the treatment was classified, with 0=no effect and 4=destruction of the plants. As can be seen from the table, destruction of the test plants was achieved.

*) sp. napus
**) sp. chamomilla

| Compounds of Invention | Post Germination | |
|---|---|---|
| | Brassica | Matricacaria |
| 2-[7-(2-Chloro-4-trifluoromethylphenoxy)-2-naphthoxy]-propanoic acid ethyl ester | 4 | 4 |
| 2-[7-(2-Chloro-4-trifluoromethylphenoxy)-2-naphthoxy]-propanoic acid ethoxyethyl ester | 4 | 4 |
| 2-[7-(3-Chloro-5-trifluoromethyl-2-pyridyloxy)-2-naphthoxy]propanoic acid ethyl ester | 4 | 4 |
| 2-[7-(2-Chloro-4-trifluoromethylphenoxy)-2-naphthoxy]- | 4 | 4 |

-continued

| Compounds of Invention | Post Germination | |
|---|---|---|
| | Brassica | Matricacaria |
| isovaleric acid ethyl ester | | |
| 2-[7-(5-Trifluoromethyl-2-pyridyloxy)-2-naphthoxy]-propanoic acid ethyl ester | 4 | 4 |
| 2-[7-(2-Chloro-4-trifluoromethylphenoxy)-2-naphthoxy]-propanoic acid 2-methoxyethyl ester | 4 | 4 |
| 2-[7-(2-Chloro-4-trifluoromethylphenoxy)-2-naphthoxy]-propanoic acid methyl ester | 4 | 4 |
| 2-[7-(2-Chloro-4-trifluoromethylphenoxy)-2-naphthoxy]-propanoic acid | 4 | 4 |
| 2-[7-(2-Chloro-4-trifluoromethylphenoxy)-2-naphthoxy]-propanoic acid 3-phenoxybenzyl ester | 4 | 4 |
| 2-[7-(2-Chloro-4-trifluoromethylphenoxy)-2-naphthoxy]-propanoic acid propargyl ester | 4 | 4 |
| 2-[7-(2-Chloro-4-trifluoromethylphenoxy)-2-naphthoxy]-propanoic acid, sodium salt | 4 | 4 |
| 2-[7-(2-Chloro-4-trifluoromethylphenoxy)-2-naphthoxy]-propanoic acid n-butyl ester | 4 | 4 |
| 2-[7-(2-Chloro-4-trifluoromethylphenoxy)-2-naphthoxy]-propanoic acid allyl ester | 4 | 4 |
| 2-[7-(2-Chloro-4-trifluoromethylphenoxy)-2-naphthoxy]-propanoic acid phenyl ester | 4 | 4 |
| 2-[7-(2-Chloro-4-trifluoromethylphenoxy)-2-naphthoxy]-thiopropanoic acid S—benzyl ester | 4 | 4 |
| 2-[7-(2-Chloro-4-trifluoromethylphenoxy)-2-naphthoxy]-thiopropanoic acid S—ethyl ester | 4 | 4 |
| 2-[7-(2-Chloro-4-trifluoromethylphenoxy)-2-naphthoxy]-propanoic acid cyclohexyl ester | 4 | 4 |
| 2-[7-(2-Chloro-4-trifluoromethylphenoxy)-2-naphthoxy]-propanoic acid 2-methylphenyl ester | 4 | 4 |
| 2-[7-(2-Chloro-4-trifluoromethylphenoxy)-2-naphthoxy]-propanoic acid 2-methylbutyl ester | 4 | 4 |
| 2-[7-(2-Chloro-4-trifluoromethylphenoxy)-2-naphthoxy]-propanoic acid 3-bromopropyl ester | 4 | 4 |
| 2-[7-(2-Chloro-4-trifluoromethylphenoxy)-2-naphthoxy]-propanoic acid amide | 4 | 4 |
| 2-[7-(2-Chloro-4-trifluoromethylphenoxy)-2-naphthoxy]-propanoic acid ethylamide | 4 | 4 |
| 2-[7-(2-Chloro-4-trifluoromethylphenoxy)-2-naphthoxy]-propanoic acid diethylamide | 4 | 4 |
| 2-[7-(2-Chloro-4-trifluoromethylphenoxy)-2-naphthoxy]-propanoic acid anilide | 4 | 4 |
| 2-[7-(2-Chloro-4-trifluoromethylphenoxy)-2-naphthoxy]-propanoic acid n-butylamide | 4 | 4 |
| 2-[7-(2-Chloro-4-trifluoromethylphenoxy)-2-naphthoxy]-propanoic acid di-n-butylamide | 4 | 4 |
| 2-[7-(2-Chloro-4-trifluoromethylphenoxy)-2-naphthoxy]-propanoic acid 2-cyanoethyl ester | 4 | 4 |
| 2-[7-(2-Chloro-4-trifluoromethylphenoxy)-2-naphthoxy]-propanoic acid N—(ethoxycarbonylmethyl)amide | 4 | 4 |
| 2-[7-(2-Chloro-4-trifluoromethylphenoxy)-2-naphthoxy]-propanoic acid N—(1-methoxycarbonylethyl)amide | 4 | 4 |
| 2-[7-(2-Chloro-4-trifluoromethylphenoxy)-2-naphthoxy]-thiopropanoic acid S—(ethoxycarbonyl)methyl ester | 4 | 4 |
| 5-O—[2-[7-(2-Chloro-4-trifluoromethylphenoxy)-2-naphthoxy]propanoic acid (1,2:3,4-bis-O—isopropylidene)]xylityl ester | 4 | 4 |
| 2-[7-(2-Chloro-4-trifluoromethylphenoxy)-2-naphthoxy]-butanoic acid ethyl ester | 4 | 4 |
| 2-[7-(2-Chloro-4-trifluoromethylphenoxy)-2-naphthoxy]-2-methylpropanoic acid ethyl ester | 4 | 4 |
| 2-(R,S)—[7-(2-Chloro-4-trifluoromethylphenoxy)-2-naphthoxy]propanoic acid [1-(S)—ethoxycarbonylethyl]ester | 4 | 4 |
| 2-(R,S)—[7-(2-Chloro-4-trifluoromethylphenoxy)-2-naphthoxy]propanoic acid [1-(R)—ethoxycarbonylethyl]ester | 4 | 4 |
| 2-[7-(4-Trifluoromethylphenoxy)-2-naphthoxy]propanoic acid ethyl ester | 4 | 4 |
| 2-[7-(2-Chloro-4-trifluoromethylphenoxy)-2-naphthoxy]propanoic acid n-propyl ester | 4 | 4 |
| 2-[7-(2-Chloro-4-trifluoromethylphenoxy)-2-naphthoxy]-propanoic acid (2,2,2-trifluoro)ethyl ester | 4 | 4 |
| 2-[7-(2-Chloro-4-trifluoromethylphenoxy)-2-naphthoxy]-propanoic acid furfuryl ester | 4 | 4 |

EXAMPLE 55

In a greenhouse, the listed plants were treated, after germination, with the cited compounds in an application quantity of 0.3 kg of active compound/ha. The compounds were sprayed for this purpose uniformly over the plants in the form of an emulsion with 500 liters of water. The treatment effect was evaluated according to the classification scheme 0 to 4, wherein 4 means total destruction and 0 means no effect. In this case, three weeks after treatment, the compounds of the invention exhibited a high selectivity with excellent effect against the weeds. The comparison compounds did not show this effect.

| Compounds Acc. to Example | Post Germination | |
|---|---|---|
| | Brassica sp. | Matricaria sp. |
| 44 | 4 | 4 |
| 45 | 4 | 4 |
| 46 | 4 | 4 |
| 47 | 4 | 4 |
| 48 | 4 | 4 |

| Compounds of Invention | Matricaria | Brassica | Viola | Stellaria | Chrysanthemum | Helianthus | Ipomoea | Echinochloa | Setaria | Rice | Wheat | Barley | Soybeans |
|---|---|---|---|---|---|---|---|---|---|---|---|---|---|
| 2-[7-(2-Chloro-4-trifluoromethylphenoxy)-2-naphthoxy]propanoic acid ethyl ester | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid ethoxyethyl ester | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid 2-methoxyethyl ester | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid methyl ester | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid propargyl ester | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid, sodium salt | 4 | 4 | 4 | 4 | 4 | 4 | 4 | 3 | 3 | 0 | 0 | 0 | 1 |
| 2-[7-(2-Chloro-4-trifluoromethylphenoxy)-2-naphthoxy]propanoic acid 2-methylbutyl ester | 4 | 4 | 4 | 4 | 4 | 4 | 4 | 3 | 3 | 0 | 0 | 0 | 1 |
| Comparison Compound (According to U.S. Pat. No. 3,979,437) 5-(2-Chloro-α,α,α-trifluoro-p-tolyloxy)-2-nitrobenzoic acid | 4 | 4 | 4 | 4 | 4 | 3 | 4 | 3 | 4 | 1 | 3 | 3 | 1 |
| Comparison Compound (According to Japanese Laid-Open Text 92,369/80) 2-[4-(5-Trifluoromethyl-2-pyridyloxy)-phenoxy]butylpropionate | 0 | 0 | 0 | 0 | 0 | 0 | 0 | 4 | 4 | 4 | 4 | 4 | 0 |

EXAMPLE 56

In a greenhouse, the compounds listed in the table were sprayed in the post-germination procedure on Brassica and Matricaria species in an application quantity of 3.0 kg of active compound/ha, emulsified in 500 liters of water. Three weeks after treatment, the result of the treatment was classified wherein 0 = no effect and 4 = destruction of plants.

| Compounds Acc. to Example | Post Germination | |
|---|---|---|
| | Brassica sp. | Matricaria sp. |
| 40 | 4 | 4 |
| 41 | 4 | 4 |
| 42 | 4 | 4 |
| 43 | 4 | 4 |
| 49 | 4 | 4 |
| 50 | 4 | 4 |
| 51 | 4 | 4 |
| 52 | 4 | 4 |
| 53 | 4 | 4 |

EXAMPLE 57

In a greenhouse, the plants listed in the table were treated, after germination, with the cited compounds in an applied amount of 0.3 kg of active compound/ha. The compounds were sprayed for this purpose uniformly over the plants as an emulsion with 500 liters of water/ha. In this case, the compounds of this invention exhibited, three weeks after treatment, a high selectivity with excellent effect against weeds. The comparison agents did not show this effect and selectivity, respectively.

| Compound of Invention According to Example | Matricaria sp. | Brassica sp. | Viola sp. | Stellaria sp. | Chrysanthemum sp. | Helianthus sp. | Ipomoea sp. | Echinochloa sp. | Setaria sp. | Rice | Wheat | Barley |
|---|---|---|---|---|---|---|---|---|---|---|---|---|
| 40, 41, 42, 43, 44, 45, 46, 47, 48 | 4 | 4 | 4 | 4 | 4 | 4 | 4 | 4 | 4 | 0 | 0 | 0 |
| Comparison Agent | | | | | | | | | | | | |
| "Blazer" | 4 | 4 | 4 | 4 | 4 | 3 | 4 | 3 | 4 | 1 | 3 | 3 |
| "Fusilade" | 0 | 0 | 0 | 0 | 0 | 0 | 0 | 4 | 4 | 4 | 4 | 4 |

| Compound of Invention According to Example | Matricaria sp. | Brassica sp. | Viola sp. | Stellaria sp. | Chrysanthemum sp. | Helianthus sp. | Ipomoea sp. | Echinochloa sp. | Setaria sp. | Rice | Wheat | Barley |
|---|---|---|---|---|---|---|---|---|---|---|---|---|
| 2-(s)-[7-(2-Chloro-4-trifluoromethylphenoxy)-2-naphthoxy]propanoic acid ethyl ester | 1 | 2 | 0 | 1 | 1 | 1 | 1 | 0 | 0 | 0 | 0 | 0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7-(aryloxy)-2-naphthoxy-alkanecarboxylic acid derivative of the Formula wherein
Z is trifluoromethyl
W is hydrogen or chlorine
X is CH or N,
$R_1$ is hydrogen or methyl,
Y is $UR_3$ or $$-N\begin{array}{c}R_9\\R_{10}\end{array}$$

U is oxygen or sulfur,
$R_3$ is H, a sodium atom, $C_1-C_6$-alkyl, methoxyethyl, ethoxyethyl, allyl, propargyl, cyclohexyl, bromopropyl, cyanoethyl, trifluoroethyl, benzyl, phenoxybenzyl, phenyl, methylphenyl, ethoxycarbonylmethyl, ethoxybarbonylethyl, or bis-0-isopropylidenexylityl,
$R_9$ is hydrogen, ethyl or butyl and
$R_{10}$ is hydrogen, ethyl, butyl, phenyl, ethoxycarbonylmethyl or methoxycarbonylethyl.

2. A racemate of a compound of claim 1.

3. A compound of claim 1 which is a separated enantiomer.

4. A 2-(R)-(7-(Aryloxy)-2-naphthoxy)propanoic acid derivative of claim 1 of the formula wherein
Z is trifluoromethyl,
X is CH or nitrogen,
Y is wherein
R is ethyl and the asymmetrical carbon atom has the R or S configuration.

5. A 7-(Aryloxy)-2-naphthoxyalkanecarboxylic acid derivative of claim 1 wherein
X is C—H, 6. A 2-(R)-[7-(Aryloxy)-2-naphthoxy]propanoic acid derivative of claim 1 wherein
X is C—H.

7. A compound of claim 1 wherein X is C—H and $R_3$ is a sodium atom.

8. 2-[7-(2-Chloro-4-trifluoromethylphenoxy)-2-naphthoxy]propanoic acid ethyl ester, a compound of claim 1.

9. 2-[7-(2-Chloro-4-trifluoromethylphenoxy)-2-naphthoxy]propanoic acid ethoxyethyl ester, a compound of claim 1.

10. 2-[7-(3-Chloro-5-trifluoromethyl-2-pyridyloxy)-2-naphthoxy]propanoic acid ethyl ester, a compound of claim 1.

11. 2-[7-(2-Chloro-4-trifluoromethylphenoxy)-2-naphthoxy]isovaleric acid ethyl ester, a compound of claim 1.

12. 2-[7-(5-Trifluoromethyl-2-pyridyloxy)-2-naphthoxy]propanoic acid ethyl ester, a compound of claim 1.

13. 2-[7-(2-Chloro-4-trifluoromethylphenoxy)-2-naphthoxy]propanoic acid 2-methoxyethyl ester, a compound of claim 1.

14. 2-[7-(2-Chloro-4-trifluoromethylphenoxy)-2-naphthoxy]propanoic acid methyl ester, a compound of claim 1.

15. 2-[7-(2-Chloro-4-trifluoromethylphenoxy)-2-naphthoxy]propanoic acid, a compound of claim 1.

16. 2-[7-(2-Chloro-4-trifluoromethylphenoxy)-2-naphthoxy]propanoic acid 3-phenoxybenzyl ester, a compound of claim 1.

17. 2-[7-(2-Chloro-4-trifluoromethylphenoxy)-2-naphthoxy]propanoic acid propargyl ester, a compound of claim 1.

18. 2-[7-(2-Chloro-4-trifluoromethylphenoxy)-2-naphthoxy]propanoic acid, sodium salt, a compound of claim 1.

19. 2-[7-(2-Chloro-4-trifloromethylphenoxy)-2-naphthoxy]propanoic acid n-butyl ester, a compound of claim 1.

20. 2-[7-(2-Chloro-4-trifluoromethylphenoxy)-2-naphthoxy]propanoic acid allyl ester, a compound of claim 1.

21. 2-[7-(2-Chloro-4-trifluoromethylphenoxy)-2-naphthoxy]propanoic acid phenyl ester, a compound of claim 1.

22. 2-[7-(2-Chloro-4-trifluoromethylphenoxy)-2-naphthoxy]thiopropanoic acid S-benzyl ester, a compound of claim 1.

23. 2-[7-(2-Chloro-4-trifluoromethylphenoxy)-2-naphthoxy]thiopropanoic acid S-ethyl ester, a compound of claim 1.

24. 2-[7-(2-Chloro-4-trifloromethylphenoxy)-2-naphthoxy]propanoic acid cyclohexyl ester, a compound of claim 1.

25. 2-[7-(2-Chloro-4-trifluoromethylphenoxy)-2-naphthoxy]propanoic acid 2-methylphenyl ester, a compound of claim 1.

26. 2-[7-(2-Chloro-4-trifluoromethylphenoxy)-2-naphthoxy]propanoic acid 2-methylbutyl ester, a compound of claim 1.

27. 2-[7-(2-Chloro-4-trifluoromethylphenoxy)-2-naphthoxy]propanoic acid 3-bromopropyl ester, a compound of claim 1.

28. 2-[7-(2-Chloro-4-trifluoromethylphenoxy-2-naphthoxy]propanoic acid amide, a compound of claim 1.

29. 2-[7-(2-Chloro-4-trifluorometthylphenoxy)-2-naphthoxy]propanoic acid ethylamide, a compound of claim 1.

30. 2-[7-(2-Chloro-4-trifluoromethylphenoxy)-2-naphthoxy]propanoic acid diethylamide, a compound of claim 1.

31. 2-[7-(2-Chloro-4-trifluoromethylphenoxy)-2-naphthoxy]propanoic acid anilide, a compound of claim 1.

32. 2-[7-(2-Chloro-4-trifluoromethylphenoxy)-2-naphthoxy]propanoic acid n-butylamide, a compound of claim 1.

33. 2-[7-(2-Chloro-4-trifluoromethylphenoxy)-2-naphthoxy]propanoic acid di-n-butylamide, a compound of claim 1.

34. 2-[7-(2-Chloro-4-trifluoromethylphenoxy)-2-naphthoxy]propanoic acid 2-cyanoethyl ester, a compound of claim 1.

35. 2-[7-(2-Chloro-4-trifluoromethylphenoxy)-2-naphthoxy]propanoic acid N-(ethoxycarbonylmethyl)amid, a compound of claim 1.

36. 2-[7-(2-Chloro-4-trifluoromethylphenoxy)-2-naphthoxy]propanoic acid N-(1-methoxycarbonylethyl)amide, a compound of claim 1.

37. 2-[7-(2-Chloro-4-trifluoromethylphenoxy)-2-naphthoxy]thiopropanoic acid S-(ethoxycarbonyl)methyl ester, a compound of claim 1.

38. 5-O-[2-? 7-(2-Chloro-4-trifluoromethylphenoxy)-2-naphthoxy]propanoic acid (1,2:3,4-bis-O-isopropylidene)]-xylityl ester, a compound of claim 1.

39. 2-[7-(2-Chloro-4-trifluoromethylphenoxy)-2-naphthoxy]butanoic acid ethyl ester, a compound of claim 1.

40. 2-[7-(2-Chloro-4-trifluoromethylphenoxy)-2-naphthoxy]-2-methylpropanoic acid ethyl ester, a compound of claim 1.

41. 2-(R,S)-[7-(2-Chloro-4-trifluoromethylphenoxy)-2-naphthoxy]propanoic acid [1-(S)-ethoxycarbonylethyl] ester, a compound of claim 1.

42. 2-(R,S)-[7-(2-Chloro-4-trifluoromethylphenoxy)-2-naphthoxy]propanoic acid [1-(R)-ethoxycarbonylethyl] ester, a compound of claim 1.

43. 2-[7-(4-Trifluoromethylphenoxy)-2-naphthoxy]propanoic acid ethyl ester, a compound of claim 1.

44. 2-[7-(2-Chloro-4-trifluoromethylphenoxy)-2-naphthoxy]propanoic acid n-propyl ester, a compound of claim 1.

45. 2-[7-(2-Chloro-4-trifluoromethylphenoxy)-2-naphthoxy]propanoic acid (2,2,2-trifluoro)ethyl ester, a compound of claim 1.

46. 2-(R)-[7-(2-Chloro-4-trifluoromethylphenoxy)-2-naphthoxy]propanoic acid ethyl ester, a compound of claim 1.

47. 2-(R)-[7-(2-Chloro-4-trifluoromethylphenoxy-2-naphthoxy]propanoic acid ethoxyethyl ester, a compound of claim 1.

48. 2-(R)-[7-(3-Chloro-5-trifluoromethyl-2-pyridyloxy-2-naphthoxy]propanoic acid ethyl ester, a compound of claim 1.

49. 2-(R)-[7-(2-Chloro-4-trifluoromethylphenoxy)-2-naphthoxy]propanoic acid 2-methoxyethyl ester, a compound of claim 1.

50. 2-(R)-[7-(2-Chloro-4-trifluoromethylphenoxy)-2-naphthoxy]propanoic acid methyl ester, a compound of claim 1.

51. 2-(R)-[7-(2-Chloro-4-trifluoromethylphenoxy)-2-naphthoxy]propanoic acid, a compound of claim 1.

52. 2-(R)-[7-(2-Chloro-4-trifluoromethylphenoxy)-2-naphthoxy]propanoic acid propargyl ester, a compound of claim 1.

53. 2-(R)-[7-(2-Chloro-4-trifluoromethylphenoxy)-2-naphthoxy]propanoic acid n-butyl ester, a compound of claim 1.

54. 2-(R)-[7-(2-Chloro-4-trifluoromathylphenoxy)-2-naphthoxy]propanoic acid allyl ester, a compound of claim 1.

55. 2-(R)-[7-(2-Chloro-4-trifluoromethylphenoxxy)-2-naphthoxy]propanoic acid 2,2,2-trifluoroethyl ester, a compound of claim 1.

56. 2-(R)-[7-(2-Chloro-4-trifluoromethylphenoxy)-2-naphthoxy]propanoic acid isopropyl ester, a compound of claim 1.

57. 2-(R)-[7-(2-Chloro-4-trifluoromethylphenoxy)-2-naphthoxy]propanoic acid n-propyl ester, a compound of claim 1.

58. 2-(R)-[7-(2-Chloro-4-trifluoromethylphenoxy)-2-naphthoxy]propanoic acid [1-(S)-ethoxycarbonylethyl] ester, a compound of claim 1.

59. 2-(R)-[7-(2-Chloro-4-trifluoromethylphenoxy)-2-naphthoxy]propanoic acid [1-(R)-ethoxycarbonylethyl] ester, a compound of claim 1.

60. A herbicidal composition comprising an amount of a compound of claim 1 and a herbicidal adjuvant.

61. A herbicidal composition of claim 60 wherein the amount of said compound is about 10–90% by weight.

62. A method of achieving a herbicidal effect on a plant comprising applying to the plant a compound of claim 1.

63. A method of selectively inhibiting the growth of grass-like plants in a crop habitat comprising applying to the grass-like plants an amount of a compound of claim 1.

64. A method of claim 65 wherein the plants are monocotyledonous or dicotyledonous weeds.

* * * * *